United States Patent [19]

Matsuo

[11] 4,116,231
[45] Sep. 26, 1978

[54] LIVING BODY FUNCTION MEASURING APPARATUS

[75] Inventor: Satoshi Matsuo, Yokohama, Japan

[73] Assignee: Tokyo Shibaura Electric Co., Ltd., Kawasaki, Japan

[21] Appl. No.: 748,403

[22] Filed: Dec. 8, 1976

[30] Foreign Application Priority Data

Dec. 10, 1975 [JP] Japan .................................. 50-147159

[51] Int. Cl.$^2$ .............................................. A61B 5/05
[52] U.S. Cl. ............................ 128/2.1 Z; 128/2.05 V
[58] Field of Search .......... 128/2.1 Z, 2.05 F, 2.05 R, 128/2.05 V

[56] References Cited

U.S. PATENT DOCUMENTS

| | | | |
|---|---|---|---|
| 3,316,896 | 5/1967 | Thomasset | 128/2.1 Z |
| 3,340,867 | 9/1967 | Kubicek et al. | 128/2.1 Z X |
| 3,556,083 | 1/1971 | Grichnik et al. | 128/2.1 Z |

OTHER PUBLICATIONS

"Nasa Tech. Brief," No. 68-10220, Jun. 1968, 2 pp.

*Primary Examiner*—Robert W. Michell
*Assistant Examiner*—Lee S. Cohen
*Attorney, Agent, or Firm*—Cushman, Darby & Cushman

[57] ABSTRACT

A heart/lung function measuring apparatus comprises a source for permitting a constant slight current of a high frequency wave of predetermined frequency to flow through a to-be-measured portion of a living body, a voltage detection section detecting a voltage loop based on the impedance of the living body area, a sample-hold circuit for sampling a predetermined level of an output signal of the voltage detection section and holding the sampled value, a peak detector for generating a detector output according to a peak voltage of the output of the detection section, a pulse generator for generating a pulse signal which is applied as a trigger signal to the sample-hold circuit according to the output of the peak detector, and a subtractor for obtaining a difference output between the output of the voltage detection section and the output of the sample-hold circuit.

3 Claims, 7 Drawing Figures

LIVING BODY FUNCTION MEASURING APPARATUS

BACKGROUND OF THE INVENTION

This invention relates to a living body function measuring apparatus, and in particular an apparatus for measuring the function of a periodically changing physiological motion area of a living body, such as the heart and lungs, without inflicting any load or influence on the living tissue and its function.

A variety of methods have been conventionally invented to measure the physiological phenomenon of a living body and reduced to practice. Among the methods an impedance method is known. This method is intended to obtain information on the function of a to-be-measured area of a living body by measuring the electric impedance of the living body area and has the advantages of being capable of measuring the impedance of the living tissue without importing any applicable influence to the living body, capable of a repetitive measurement and capable of a continuous measurement for a lengthy time period.

To explain more in detail the impedance method is intended to measure the function of the heart and lungs, i.e., physiological phenomena on a respiratory or circulatory system, as a variation of electric impedance by permitting a constant slight current of predetermined high frequency to flow through a to-be-measured area of a living body, that is to say, to measure a predetermined living tissue impedance $Z_0$ and an impedance variation $\Delta Z$ which varies by respiration or circulation. Such an impedance method finds the following clinical applications:

(a) the measurement of a cardiac stroke volume
(b) measurement and monitoring of intrathoracic fluid volumes
(c) measurement and monitoring of an inspire/expire pattern, the number of respirations and the relative change of an inspire/expire amount
(d) monitoring of a patient under artificial respiration
(e) measurement of a limb bloodstream To realize such an impedance method a living body measuring apparatus as shown in FIG. 1 has been put to practice. In FIG. 1, reference numeral 1 is a living body (a subject) to be measured, and 2 is a high frequency wave constant current source for generating a slight current of constant high frequency. 3 and 6 are current applying electrode strips struck to the subject 1. Through the electrode strips 3, 6 a constant slight current is applied from the constant current source 2 to the living body 1. The living body 1 involves a living tissue impedance $Z_0$ and an impedance $\Delta Z$ corresponding to a variation in a physiological motion such as respiration, pulsation etc. A voltage drop due to the presence of such impedances is detected through the voltage detecting electrode strips 4, 5 stuck to the subject 1.

Because an electric current applied to the electrode strips 3, 6 is constant current of predetermined frequency it is possible to obtain a voltage proportional to the impedance of the living body 1 by means of electrode strips 4, 5. Such a voltage is, after amplified at a high-gain AC amplifier 7, supplied to a detector 8 where it is detected and smoothed. The output of the detector 8 becomes a ripple voltage corresponding to a living body impedance between the electrode strips 4 and 5. As shown in FIG. 2, for example, the value of the impedance variation $\Delta Z$ is maximal at a maximum inhalation time A in a respiration curve and, since at the end of the expiration phase B the value of $\Delta Z$ becomes minimal, the DC and AC components of a ripples voltage delivered from the detector 8 are considered, as shown in FIG. 3, as corresponding to a living tissue impedance $Z_0$ and impedance variation $\Delta Z$. In consequence, the living tissue impedance $Z_0$ is considered to be a living body impedance when the value of the impedance variation $\Delta Z$ in FIG. 3 is minimal, for example, at the end of the expiration phase B in the respiration curve.

The living tissue impedance $Z_0$ and impedance variation $\Delta Z$ are of importance as parameters for measuring the function of the living body and it is, therefore, necessary to separately obtain from the output of the detector 8 information corresponding to the impedance $Z_0$ and impedance variation $\Delta Z$. To this end, the output of the detector 8 is delivered to a sample-hold circuit 9 and an external trigger signal is manually applied to the sample-hold circuit 9 in a state in which respiration is stopped at the end of the expiration phase B in FIG. 2 or an external trigger signal is applied to the sample-hold circuit at a time when a maximum expiration level is considered to be attained while observing the output waveform of $\Delta Z$. Thereafter, a voltage $E(Z_0)$ corresponding to the living tissue impedance $Z_0$ is held in the sample-hold circuit 9. This voltage $E(Z_0)$ is delivered as information $Z_0$ to a subtraction circuit 10 where it is subtracted from an output voltage $E(Z_0+\Delta Z)$ corresponding to the impedance $Z_0+\Delta Z$ of the detector 8 to obtain a voltage $E(\Delta Z)$ corresponding to $\Delta Z$. The voltage corresponding to $\Delta Z$ is taken out after amplified at a DC amplifier 11.

Although in the above-mentioned apparatus respiration is stopped at the end of the expiration phase in obtaining a trigger signal, the stopping of respiration imparts a great burden to a patient suffering from a respiratory disease. Furthermore, the subject does not always accurately stop respiration at a maximum expiration time. If respiration is voluntarily stopped, there is a possibility that a data different from that in an ordinary time will be obtained. Even in the method for forming an external trigger signal while observing the waveform of $\Delta Z$, it is difficult to accurately deliver an external trigger signal at a maximum exhalation time. Therefore, a reliable measured data can not obtained due to these reasons and this sometimes leads to a possible erroneous diagnosis.

It is accordingly the object of this invention to provide a living body function measuring apparatus capable of accurately measuring a living body impedance in a normal state without imparting any burden or influence to a living body or its function.

According to this invention there is provided a living body function measuring apparatus comprising means for permitting a slight constant current of high frequency wave of predetermined frequency to flow to a to-be-measured area of a living body, a voltage section for detecting a voltage drop based on the impedance of the living body area, a sample-hold circuit for sampling a predetermined level of the output signal of the voltage detection section and holding the sampled value, means for applying a trigger signal to the sample-hold circuit according to the above-mentioned predetermined level, and means for obtaining a difference output between the output of the voltage detection section and the output of the sample-hold circuit.

DETAILED DESCRIPTION OF THE PREFERRED EMBODIMENTS

Figure 4:
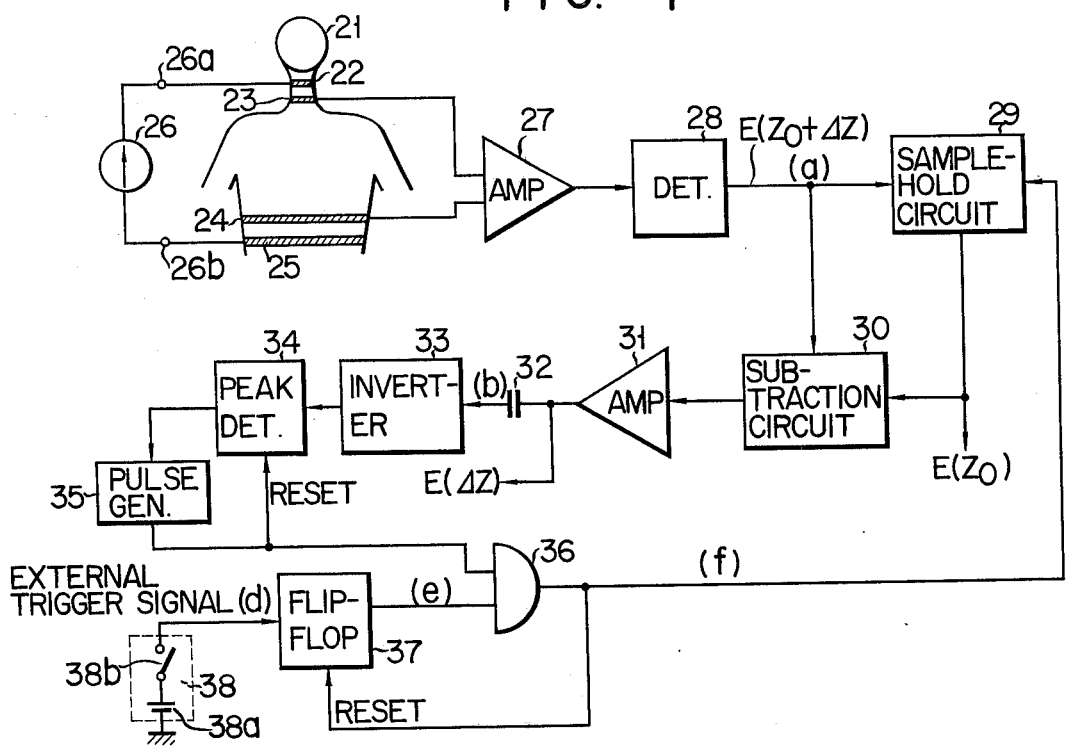
FIG. 4 is a block diagram showing one embodiment of this invention.

In FIG. 4 a pair of electrode strips 22, 23 are stuck at a predetermined interval around the neck of a living body 21 (a subject). Likewise, a pair of electrode strips 24, 25 are stuck at a predetermined interval around the trunk of the subject 21. In this case, it is preferred that the paired electrode strips 22 and 23, and 24 and 25, be spaced more than 3 cm apart with respect to each other. The electrode strips 22 and 25 are connected respectively through terminals 26a and 26b to a high-frequency constant source 26 for generating a slight, constant frequency current.

Figure 5:
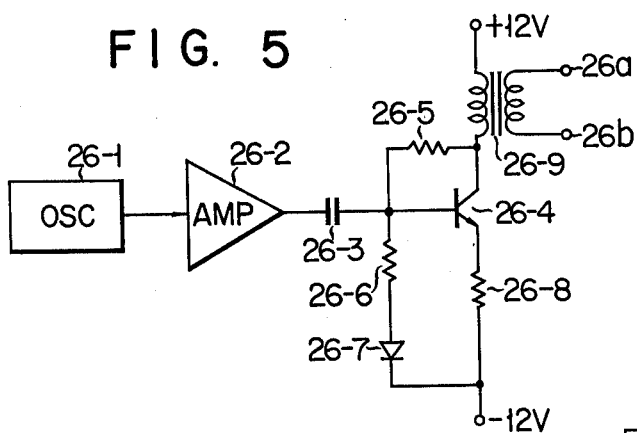
FIG. 5 is a circuit diagram showing one form of a high frequency wave, slight constant current source in FIG. 4.

The constant current source 26 comprises a circuit arrangement as shown in FIG. 5. The output of an oscillator 26-1 having an oscillation frequency of, for example, 50 kHz is, after amplified at an amplifier 26-2, applied through a coupling capacitor 26-3 to the base of a transistor 26-4. A bias resistor 26-5 is connected between the collector and the base of the transistor 26-4 and a series circuit of a bias resistor 26-6 and temperature compensation diode 26-7 is connected between the base and a −12V power supply terminal. The collector of the transistor 26-4 is connected through a primary winding of a transformer 26-9 to a +12V power supply terminal. Both the ends of a secondary winding of the transformer 26-9 are connected to the output terminals 26a and 26b, respectively. The transformer 26-9 is used to involve a very great impedance when the constant current source 26 is viewed from the side of the output terminals 26a and 26b.

Reverting to FIG. 4 the voltage detection electrode strips 23 and 24 are connected to the input terminal of a high gain AC amplifier 27. The output of the AC amplifier 27 is supplied to a detector 28 where it is detected and smoothed. The output of the detector 28 is coupled to a sample-hold circuit 29 and subtraction circuit 30. The subtraction circuit 30 is adapted to subtract the output of the sample-hold circuit 29 from the output of the detector 28. A difference output from the subtraction circuit 30 is, after amplified at a DC amplifier 31, supplied through a coupled capacitor 32 to an inverter 33. The output of the inverter 33 is connected to a peak detector 34, and the output of the peak detector 34 is connected to the input terminal of a pulse generator 35. As the peak detector 34 use may be made of a peak detector as disclosed, for example, in Operational Amplifiers—Design and Applications—, Editors: G. Tobey, J. Graeme, L Huelsman p358, FIG. 9.28, publisehd in 1971 from McGrawHill Book Company.

The output of the pulse generator 35 is connected to a reset terminal of the peak detector 34 and to one input terminal of an AND circuit 36. The set output of a flip-flop 37 is connected to the other terminal of the AND circuit 36. An external trigger signal from an external trigger signal generator 38 is supplied to the input of the flip-flop 37. The output of the AND circuit 36 is connected to the reset terminal of the flip-flop 37 and to a trigger input terminal of the sample-hold circuit 29. In the external trigger signal generator 38 is connected the positive electrode of a DC power supply 38a to the input of the flip-flop 37 through a manual switch 38b.

Figure 6:
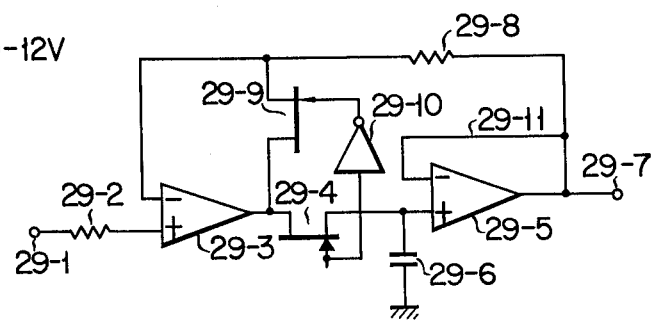
FIG. 6 is one form of the sample-hold circuit in FIG. 4.

The sample-hold circuit 29 is constructed as shown, for example, in FIG. 6. In FIG. 6 the output of the detector 28 is supplied to an input terminal 29-1 and then to a positive terminal of a first operational amplifier 29-3 through a resistor 29-2. The output of the operational amplifier 29-3 is fed to a positive terminal of a second operational amplifier 29-5 through a first field effect transistor (FET) switch 29-4. The positive terminal of the second operational amplifier 29-5 is grounded through a capacitor 29-6. The output of the operational amplifier 29-5 is coupled through an output terminal 29-7 to the subtraction circuit 30 and fed back to a negative terminal of the first operational amplifier 29-3 through a feedback loop including a resistor 29-8. The output of the operational amplifier 29-3 is fed back to the negative input terminal of the operational amplifier 29-3 through a second FET switch 29-9. A trigger input terminal of the FET switch 29-4 is connected through an inverter 29-10 to a trigger input terminal of the FET switch 29-9. The trigger input terminal of the FET switch 29-4 is connected to the output terminal of the AND circuit 36. The output of the second operational amplifier 29-5 is fed back to a negative input terminal of the second operational amplifier 29-5 through a feedback loop 29-11. When a trigger signal is supplied in a sampling mode to the FET switch 29-4, the FET switch 29-4 is rendered ON and the switch 29-9 is rendered OFF. A maximum current of the operational amplifier 29-3 flows through the switch 29-4 until the capacitor 29-6 is completely charged. In the hold mode the switch 29-4 is rendered OFF and the switch 29-9 is rendered ON. The switch 29-9 constitutes a feedback loop of the operational amplifier 29-3. In this state, a voltage held at the capacitor 29-6 is delivered from the output terminal 29-7.

Figure 1:
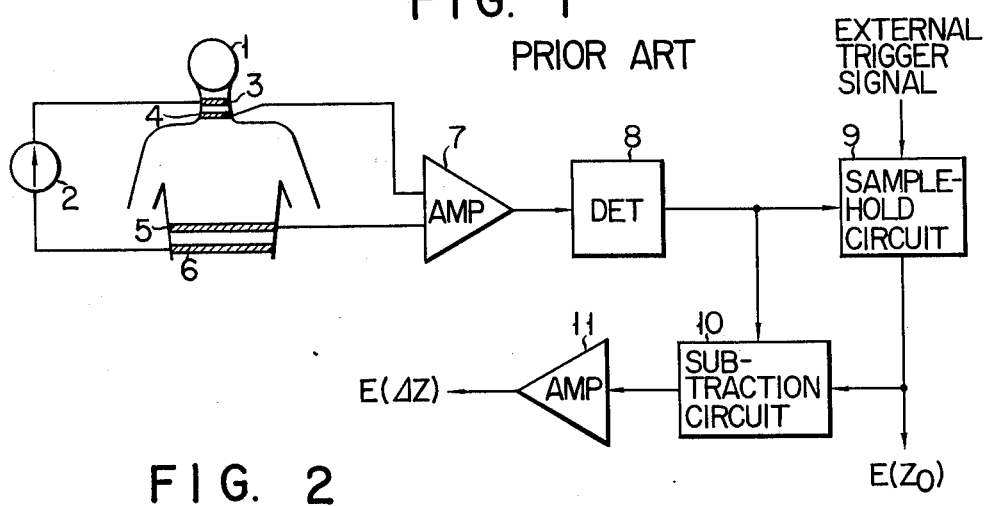
FIG. 1 is a block diagram showing a conventional living body function measuring apparatus by way of example.
Figure 2:
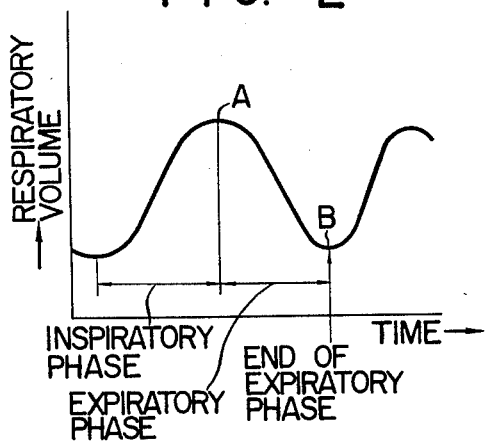
FIG. 2 is a curve showing a time variation of inhalation.
Figure 3:
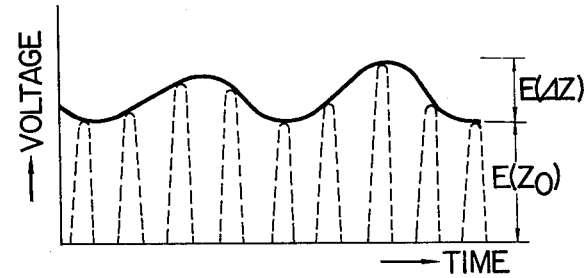
FIG. 3 is a curve showing a time variation of a living body impedance.
Figure 7:
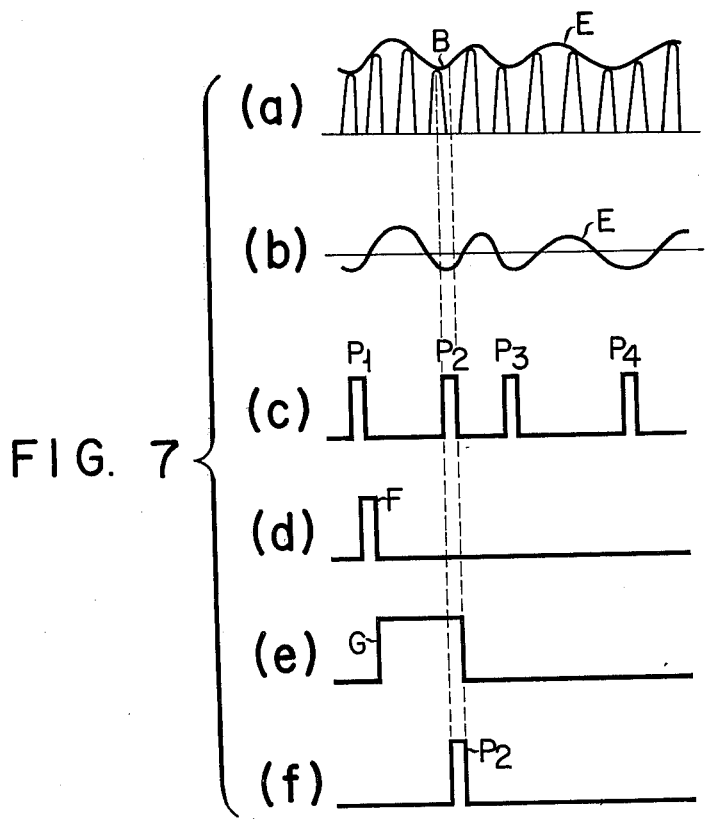
FIG. 7 is a signal waveform for explaining the operation of the circuit in FIG. 4.

If in the apparatus shown in FIG. 4 a slight current of a high frequency wave of predetermined frequency flows from the constant current source 26 through the electrode strips 22 and 25 to a to-be-measured portion of the living body 21, a voltage drop corresponding to the impedance of the living body 21 appears between the electrodes 23 and 24. This voltage is applied to the input of the AC amplifier 27. The voltage signal based on the impedance of the living body 21 is, after amplified at the AC amplifier 27, fed to the detector 28 where it is detected and smoothed. As a result, a high frequency component is eliminated to obtain a ripple voltage as indicated by an envelope curve E in FIG. 7a. As explained in FIG. 3 the ripple voltage is a sum $E(Z_0+\Delta Z)$ obtained by adding together a DC voltage component corresponding to a predetermined impedance $Z_0$ of the living tissue and an AC voltage component corresponding to an impedance $\Delta Z$ which corresponds to a variation in the periodically changing function of the living body. The output voltage of the detector 28 is fed to the sample-hold circuit 29 and subtraction circuit 30. At the initial state no external trigger signal is supplied to the flip-flop circuit 37 and thus no gate signal is supplied from the flip-flop 37 to the AND circuit 36. Consequently, no trigger signal is supplied from the AND circuit 36 to the sample-hold circuit 29 and thus no output is delivered from the sample-hold circuit 29 to the subtraction circuit 30. The output voltage of the detector 28 is supplied through the subtractor 30 to the DC amplifier 31 where it is amplified. The output of the amplifier 31 is supplied to the coupling capacitor 32. A DC component in the output voltage signal of the DC amplifier 31 is blocked at the coupling capacitor 32 and only an envelope voltage E (FIG. 7b) corresponding to the impedance variation $\Delta Z$ is inputted to the inverter 33. The inverter 33 inverts the polarity of the envelope voltage E for supply to the peak detector 34 and it is used to detect, for example, the end of the expiratory phase B in a respiration curve in FIG. 2 at the peak detector 34. In consequence, a peak detector output corresponding to a minimum value in each cycle of the envelope curve E in FIG. 7b is obtained from the peak detector 34. If the peak detection output is applied to the pulse generator 35, pulses $P_1$, $P_2$, $P_3$ and $P_4$ as shown in FIG. 7c are obtained from the pulse generator 35. The output of the pulse generator 35 causes the peak detector 34 to be reset and it is also applied to the one input terminal of the AND circuit 36.

When the switch 38b of the trigger signal generator 38 is closed and then opened by an operator to cause one external trigger pulse F to be supplied to the input terminal of the flip-flop 37 at the time shown in FIG. 7d, the flip-flop 37 is set according to the fall of the external trigger pulse F and a pulse output G shown in FIG. 7e is obtained from the flip-flop 37. The output G of the flip-flop 37 is applied to the other input terminal of the AND circuit 36 and the gate of the AND circuit 36 is opened. When in this state a peak detection pulse $P_2$ as shown, for example, in FIG. 7c is applied from the pulse generator 35 to one input terminal of the AND circuit 36 it is delivered as a trigger signal to the sample-hold circuit 29 through the AND circuit 36 (FIG. 7f). When the trigger pulse $P_2$ shown in FIG. 7f falls at the output side of the AND circuit 36 an input to the reset terminal of the flip-flop 37 falls to cause the flip-flop 37 to be reset. As a result, the output of the flip-flop 37 is regained as shown in FIG. 7e. Since in this way the external trigger pulse F is merely used to set the flip-flop 37, it does not matter if the external trigger pulse F is applied in a manner to have any relation to the phase of a peak value of the envelope voltage E shown in FIG. 7b.

When the trigger pulse $P_2$ is supplied from the AND circuit 36 the sample-hold circuit 29 samples an output volate at that time of the detector 28, i.e., a voltage at the end of the expiretory phase B so as to be held. This voltage is a voltage $E(Z_0)$ when the impedance variation $\Delta Z$ is minimal and thus a voltage corresponding to the living tissue impedance $Z_0$. This voltage is a measured data as obtained when the subject is in normal state, without stopping respiration. Thus, the measured value is considered as very reliable. If at the subtraction circuit 30 the output voltage $E(Z_0)$ of the sample-hold circuit 29 is subtracted from the output voltage $E(Z_0 + \Delta Z)$ of the detector 28 a component corresponding to the living tissue impedance $Z_0$ is not included in the output voltage of the subtractor 30, and the output voltage of the subtractor 30 becomes a voltage component $E(\Delta Z)$ purely corresponding to the impedance variation $\Delta Z$. The output voltage $E(Z_0)$ of the sample-hold circuit 29 and output voltage $E(\Delta Z)$ of the DC amplifier 31 so obtained is used as a state parmeter voltage signal representing the state of the respiratory system of the subject 21.

Although the function measurement of the respiratory system of the subject has been explained, it is also possible to measure the other physiological functions such as the function of a circulatory system.

From the impedance variation of the physiologically varying living tissue the living tissue impedance at its peak point can be automatically and accurately fixed as a living tissue impedance $Z_0$. It is therefore possible to accurately measure the impedance variation $\Delta Z$ also. Since, for example, the subject does not need to stop respiration a load to the living tissue is alleviated and it is possible to provide a living tissue function measureing apparatus capable of obtaining a diagnostically effective measuring signal.

Since in the above-mentioned embodiment the upper side band component of the high frequency impedance signal is detected at the detector 28, the inverter 33 is used at the preceding stage of the peak detector 34. If, however, the lower side band component of the impedance signal is detected at the detector 28 or if the DC amplifier 31 is of a phase inversion type the inverter 33 is unnecessary.

If the living tissue impedance $Z_0$ is updated and held using a circuit capable of updating and holding the level of a sampled signal based on the trigger signal, it is not necessary to provide the flip-flop 37 and AND circuit 36. Although the sample-hold circuit 29 is shown as of an analog type, a digital type may also be used.

What is claimed is:

1. A living body function measuring apparatus comprising means for permitting a constant slight current of a high frequency wave of predetermined frequency to flow through a to-be-measured portion of the living body; means for detecting a voltage drop based on an impedance of the living body portion; a sample-hold circuit means connected to said detecting means for sampling a predetermined level of an output signal of the voltage detecting means and holding the sampled value; means connected to said detecting means and said sample-hold circuit means for obtaining a difference output between the output of said voltage detecting means and the output of the sample-hold circuit means; and means for applying automatically a trigger signal to the sample-hold circuit means according to a peak level of said output signal of the difference obtaining means, the peak level corresponding to an end of an expiratory phase of the living body.

2. A living body function measuring apparatus according to claim 1, in which said trigger signal applying means includes a peak detector means connected to said difference obtaining means for generating an output according to a peak voltage of an output of said difference obtaining means corresponding to the end of the expiratory phase and pulse signal generating means connected to said peak detector means for generating a pulse signal as a trigger signal to said sample-hold circuit means according to the output of said peak detector means.

3. A living body function measuring apparatus according to claim 2, in which said pulse signal generating means has a pulse generator means connected to said peak detector means for receiving the output of the peak detector means for generating a corresponding output pulse signal according to the output of said peak detector means, an AND circuit having one terminal connected to an output terminal of the pulse generator means, a flip-flop having an output terminal connected to the other terminal of the AND circuit and adapted to be set by an external trigger signal, and means for clearing an output of said flip-flop by the output of said AND circuit, an output of said AND circuit being connected to said sample-hold circuit means for supply as a trigger signal to said sample-hold circuit means.

* * * * *